(12) United States Patent
Kropfeld

(10) Patent No.: US 6,421,410 B1
(45) Date of Patent: Jul. 16, 2002

(54) COMPUTED TOMOGRAPHY APPARATUS WITH SHADOWGRAM PRESENTATION

(75) Inventor: Helmut Kropfeld, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 35 days.

(21) Appl. No.: 09/721,197

(22) Filed: Nov. 22, 2000

(30) Foreign Application Priority Data

Nov. 26, 1999 (DE) .......................................... 199 57 127

(51) Int. Cl.[7] .................................................. A61B 6/03
(52) U.S. Cl. ............................................ 378/4; 378/901
(58) Field of Search ................................. 378/4, 15, 901

(56) References Cited

U.S. PATENT DOCUMENTS

| | | | |
|---|---|---|---|
| 5,247,556 A | | 9/1993 | Eckert et al. .................. 378/4 |
| 5,315,628 A | | 5/1994 | Guendel ....................... 378/20 |
| 5,377,250 A | * | 12/1994 | Hu .............................. 378/14 |
| 5,430,783 A | * | 7/1995 | Hu et al. ...................... 378/15 |
| 5,974,108 A | * | 10/1999 | Taguchi et al. ............... 378/15 |

* cited by examiner

Primary Examiner—David V. Bruce
(74) Attorney, Agent, or Firm—Schiff Hardin & Waite

(57) ABSTRACT

In a computed tomography apparatus with a detector array whose output signals are processed into shadowgrams in a computer, for which purpose a relative displacement ensues between the measuring unit composed of x-ray source and a detector array and the patient support in the longitudinal direction of the support, the output signals are acquired by the computer. A convolution of the output signals ensues in the longitudinal support direction (Z-direction) during the scanning, with values extrapolated from measured values also being used in the calculation. A lagging of the shadowgram presented on the monitor compared to the measuring unit is thus avoided.

2 Claims, 1 Drawing Sheet

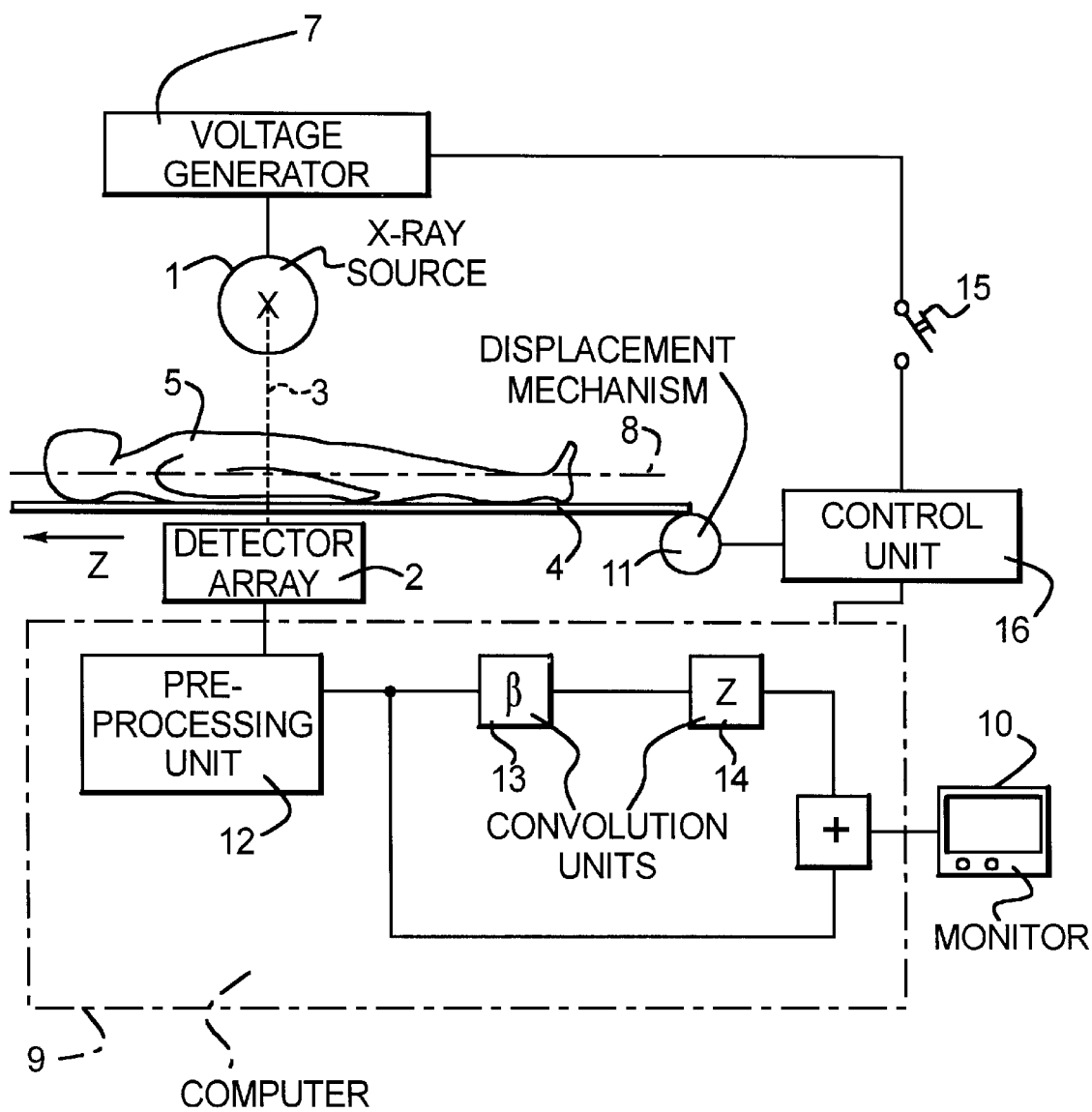

COMPUTED TOMOGRAPHY APPARATUS WITH SHADOWGRAM PRESENTATION

BACKGROUND OF THE INVENTION

1. Field of the Invention

The present invention is directed to a computed tomography apparatus of the type having a detector array whose output signals are processed into shadowgrams in a computer, for which purpose a relative displacement ensues between the measuring unit composed of an x-ray source and detector array, and the patient support in the longitudinal direction of the support, and the output signals are acquired by the computer at a predetermined angular position of the measuring unit.

2. Description of the Prior Art

In a computed tomography apparatus of the third generation, it is known to rotate the measuring unit around the system axis by 360° for the presentation of a specific slice of the examination subject and to calculate the tomogram from the output signals of the detector array. For defining the slice that is to be tomographically presented, the measuring unit is locked against rotation in a predetermined angular position, and a relative displacement between the measuring unit and the patient support ensues proceeding from a start position. The length for this relative displacement is preset. Subsequently, radiation is triggered and the output signals of the detector array are acquired by the computer during the scanning. The shadowgram is calculated from the intermediately stored and partially processed output signals of the detector array only after the preset relative displacement, that corresponds to the desired length of the shadowgram has been traversed. The calculation of the shadowgram, therefore ensues only after the patient support has reached the preset final position.

Presetting the length of the shadowgram means an additional operating procedure. Since the presentation of the shadowgram ensues only after the measurement, it is possible that a measurement that is either too short or too long can occur. In the former instance, the registration of the shadowgram must be repeated; the patient is exposed to unnecessary radiation in both instances.

It is also known to fashion a computed tomography apparatus of the third or fourth generation such that a shadowgram can be produced simultaneously with the exposure (German OS 41 03 588).

Moreover, German PS 42 23 430 discloses a computed tomography apparatus with a detector array whose output signals are also processed to shadowgrams in a computer in addition to being processed into tomograms, with a relative displacement ensuing between the measuring unit and the patient support in the longitudinal direction of said support, and the output signals are acquired by the computer at predetermined angular positions of the measuring unit. A convolution of the output signals in longitudinal direction (Z-direction) of the support ensues according to the following equation:

$$b_l(k) = \sum_{K=-n/2}^{n/2} U_l(k - K) * h(K)$$

wherein

\* means "convolved with"

l the index in the β-direction k the index in the Z-direction

κ the count index for the convolution $U_l(k)$ the readings convolved in the β-direction (measurement of the attenuation values of a slice)

$U_l(k_r)$ the most recently registered reading $b_l(k)$ the readings additionally convolved in the Z-direction h the convolution kernel n the degree of the convolution kernel β the longitudinal direction of the detector array.

SUMMARY OF THE INVENTION

An object of the present invention is to provide a teaching for a computed tomography apparatus with improved image quality in the production of shadowgrams.

This object is inventively achieved in a computed tomography apparatus wherein the shadowgram is already reproduced on a monitor during the relative displacement between the patient support and the measuring unit, the shadowgram being reproduced according to the progress of this relative displacement. The measuring system can be locked in a predetermined angular position, so that only a shadowgram can be produced in the measurement. However, the measuring system also can rotate around the examination subject during the exposure, so that a shadowgram and a tomogram are simultaneously generated. The physician can end the measurement when the desired field of measurement is recognized in the shadowgram.

DESCRIPTION OF THE DRAWING

The single FIGURE is a schematic block diagram of an embodiment of a computed tomography apparatus constructed and operating in accordance with the principles of the present invention.

DESCRIPTION OF THE PREFERRED EMBODIMENTS

The drawing shows a measuring unit composed of an x-ray source 1 and a detector array 2 that extends perpendicular to the plane of the drawing and is composed of a row of detector elements. The detector array 2 is struck by a fan-shaped X-ray beam 3 whose fan plane proceeds perpendicular to the plane of the drawing and that penetrates a patient 5 lying on a patient support 4. The x-ray source 1 is powered by a voltage generator 7.

For producing computed tomograms, a predetermined slice of the patient 5 is scanned by rotating the measuring unit 1, 2 together with the X-ray beam 3 through 360° around a system axis 8. A computer 9 calculates a tomogram from the output signals of the detector array 2 that are thereby generated and effects the playback thereof on a monitor 10.

Shadowgrams also can be produced with the illustrated computed tomography apparatus for determining a slice to be imaged in a tomogram. To this end, the output signals are acquired by the computer 9 at a predetermined angular position of the measuring unit 1, 2, and a relative displacement between the measuring unit 1, 2 and the patient support 4 ensues by shifting the patient support 4 in the longitudinal direction, i.e. in the Z-direction, with a displacement mechanism 11. At the same time, the measuring unit 1, 2 also can rotate around the patient 5, so that a computed tomogram is generated simultaneously with the shadowgram.

The computer 9 contains a pre-processing unit 12 that is followed by a convolution unit 13 for the convolution in the β-direction and a convolution unit 14 for the convolution in the Z-direction. The β-direction is the longitudinal direction of the detector array 2. A superimposition of the convoluted and the non-convoluted information and a presentation of the shadowgram on the monitor 10 follow.

The convolution in the Z-direction is implemented with direct convolution, according to the following equation:

$$b_l(k) = \sum_{K=-n/2}^{n/2} U_l(k-K) * h(K)$$

wherein
* means "convolved with"
l the index in the β-direction
k the index in the Z-direction
κ the count index for the convolution
$U_l(k)$ the readings convolved in the β-direction (measurement of the attenuation values of a slice)
$U_l(k_r)$ the most recently registered reading
$b_l(k)$ the readings additionally convolved in the Z-direction
h the convolution kernel
n the degree of the convolution core
β the longitudinal direction of the detector array 2.

After every convolution step, the data $b_1(0)$ through $b_1(k)$ are superimposed with a line-by-line weighting and are displayed at the monitor 10.

The last n/2 lines represent only an intermediate result since the readings required therefor are not yet available. At a specific point in time, let the most recently registered reading be $Ul(k_r)$. With the above equation, the last reading convolved in the Z-direction that is completely based on registered readings $U_l(k)$ would thereby derive as $b_l(k=k_r-n/2)$, i.e. lagging by n/2 image lines. In order to nonetheless also obtain a presentation for the last n/2 image lines, the value zero was assigned to previously lacking readings $U_l(k)$ in the above equation. An intermediate result with inferior image quality is thus displayable for these image lines.

According to the invention, the image quality of the most recently registered n/2 image lines is improved in that values from existing readings $U_l(k)$ with $k \leq k_r-n/2$ are extrapolated instead of the value zero for $U_l(k)$ with $k>k_r-n/2$. In the simplest case, $U_l(k)$ with $k>k_r-n/2$ are thereby replaced by $U_l(k_r)$. A clear quality improvement for the most recently registered n/2 image lines can thus be achieved. The last n/2 readings $b_1$ convoluted in Z-direction are thus re-calculated for the most recently registered n/2 image lines and, thus, are approximated step-by-step to their final value.

A realization with "fast convolution", i.e. calculation using the discrete Fourier transformation and its inverse, thus is not precluded. The registration of a shadowgram ensues by the physician pressing a key 15. The radiation is switched on as a result, and the relative displacement between the measuring unit 1, 2 and the patient support 4 is initiated via a control unit 16. The computer 9 calculates the respective shadowgram synchronously with the relative displacement and effects the playback thereof on the monitor 10 in real time. When the physician recognizes the desired field of measurement in this shadowgram, the physician releases the key 15 and the generation of the shadowgram is ended.

According to the invention, all measured readings contribute to the calculation of images, so that the physician recognizes the intended measuring region early from the shadowgram and ends the exposure correspondingly early. The radiation stress on the patient is reduced as a result.

The above-described exemplary embodiment is a CT apparatus of the third generation, i.e. the X-ray source and the detector rotate in common around the system axis during the image generation. The invention, however, can also be employed in CT apparatus of the fourth generation wherein only the X-ray source rotates and interacts with a stationary detector ring. Differing from the exemplary embodiment, further, the detector system that is employed can be a multi-line detector system. Moreover, the invention is not limited to the medical application of a CT apparatus according to the exemplary embodiment. It also can be employed outside medicine, for example in baggage inspection or in examination of materials.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising:

an x-ray source which emits x-rays;

a detector array on which said x-rays are incident and which emits output signals dependent on x-rays incident thereon, said detector array having a longitudinal direction β;

a patient support adapted to receive an examination subject thereon and having a longitudinal direction Z;

a displacement arrangement for producing a relative displacement between said x-ray source and said detector array, and said patient support, in said Z-direction with output signals from said detector array being acquired with said x-ray source and said detector array in a predetermined angular position around said patient support; and a computer to which said output signals are supplied, said computer convolving said output signals in said Z-direction according to $$b_l(k) = \sum_{\kappa=-n/2}^{n/2} U_l(k-\kappa) * h(\kappa)$$

and extrapolating missing readings $U_l(k-\kappa)$ with $(k-\kappa)>k_r$ from existing readings $U_l(k-\kappa)$ with $(k-\kappa) \leq k_r$, and wherein
* means "convolved with"

l is the index in the β-direction, k is the index in the Z-direction,

κ is the count index for the convolution, $U_l(k)$ are readings convolved in the β-direction representing measurement of the attenuation, values of a slice of the subject, $U_l(k_r)$ is a most recently registered reading, $b_l(k)$ are readings additionally convolved in the Z-direction, h is the convolution kernel, n is the degree of the convolution kernel.

2. Computed tomography apparatus as claimed in claim 1, wherein said computer extrapolates said missing readings by replacing missing readings $U_l(k-\kappa)$ with $(k-\kappa)>k_r$ with $U_l(k_r)$.

* * * * *